United States Patent
Derby, Jr.

(10) Patent No.: US 8,414,493 B2
(45) Date of Patent: Apr. 9, 2013

(54) AUTOMATIC GAIN CONTROL IN MEDICAL DIAGNOSTIC ULTRASOUND IMAGING

(75) Inventor: William M. Derby, Jr., Bethlehem, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1229 days.

(21) Appl. No.: 11/897,420

(22) Filed: Aug. 29, 2007

(65) Prior Publication Data

US 2009/0062648 A1   Mar. 5, 2009

(51) Int. Cl.
*A61B 8/08* (2006.01)

(52) U.S. Cl. .................. 600/442; 600/459

(58) Field of Classification Search .......... 600/437, 600/440, 442, 446, 458; 73/584, 596, 609; 382/128, 270–274
See application file for complete search history.

(56) References Cited

U.S. PATENT DOCUMENTS

| | | | |
|---|---|---|---|
| 4,852,576 A | 8/1989 | Inbar et al. | |
| 5,307,815 A * | 5/1994 | Gatzke et al. | 600/437 |
| 5,573,001 A | 11/1996 | Petrofsky et al. | |
| 5,579,768 A * | 12/1996 | Klesenski | 600/442 |
| 5,594,807 A * | 1/1997 | Liu | 382/128 |
| 5,722,412 A * | 3/1998 | Pflugrath et al. | 600/459 |
| 6,579,238 B1 | 6/2003 | Simopoulos et al. | |
| 6,875,178 B2 | 4/2005 | Phelps et al. | |
| 2003/0236459 A1* | 12/2003 | Loftman et al. | 600/437 |
| 2004/0015079 A1* | 1/2004 | Berger et al. | 600/437 |

OTHER PUBLICATIONS

Natarajan. Automatic Gain Control for a Small Portable Ultrasound Device. Department of Electrical Engineering and Computer Science, Massachusetts Institute of Technology. May 23, 2001.*
"Acuson P10 Unveiled at RSNA," SIEMENS; Aug. 14, 2007; www.siemens.com/webapp/wcs/stores/Printableview.

* cited by examiner

*Primary Examiner* — Parikha Mehta

(57) ABSTRACT

Gain is adjusted automatically in ultrasound imaging. The average of signals regardless of type of reflector (e.g., tissue or fluid) is determined, such as from all data in a frame of data representing a scanned region. The gain is set based on the difference between the average and the target. The gain offset is used with or without other gain limitations for analog, digital, or both analog and digital amplifiers. Given less computational expense, a same processor performing image processing functions may be used to also determine gain. A handheld ultrasound scanner with less computation bandwidth may implement the automatic gain adjustment. Given limited space for input devices, a depth gain may be provided without sliders or other depth based gain input.

21 Claims, 1 Drawing Sheet

AUTOMATIC GAIN CONTROL IN MEDICAL DIAGNOSTIC ULTRASOUND IMAGING

BACKGROUND

The present invention relates to medical imaging. In particular, a system and method of automatic gain control is provided.

In many ultrasound machines, an overall gain and time gain adjustments are provided. The user rotates a knob to control the overall gain. A plurality of sliders, such as adjacent a side of a display screen, allow different gains to be applied to signals from different depths. A skilled operator increases or decreases the depth dependent gains along with the overall gain to produce an optimal image. For example, the user may adjust the gains to provide similar brightness at different depths. The user may set the overall brightness at a level desired by the user, such as to provide tissue signals at a mid or lower than middle level brightness.

U.S. Pat. No. 6,579,238 discloses an automatic gain algorithm. Signals from tissue are identified. Using the tissue signals, a surface or slowly varying spatial gain is determined to set the mean tissue signal at a target level. However, the identification of the tissue signals and/or the surface fitting may be computationally expensive.

BRIEF SUMMARY

By way of introduction, the preferred embodiments described below include systems, methods, computer readable media, and instructions for automatically adjusting gain. A feedback value, such as an average of signals regardless of type of reflector (e.g., tissue or fluid), is determined. The data used is from any collection of data, such as from all data in a frame of data representing a scanned region. The gain is set based on the difference between the feedback value (e.g., average) and a target, such as a single gain offset being determined for the entire image. The gain offset is used with or without other gain limitations to increase or decrease the signal level of analog, digital, or both analog and digital amplifiers.

Given less computational expense, a same processor performing image processing functions (e.g., detection, filtering, persistence, and/or scan conversion) may be used to also determine gain. For example, a handheld ultrasound scanner with less computation bandwidth due to power or size limitations may implement the automatic gain adjustment. Given limited space for input devices and restricted operation constraints, a depth gain may be provided without sliders or other depth based gain input.

In a first aspect, a system for automatic gain control is provided in medical diagnostic ultrasound imaging. A processor connects with a transducer. The processor is operable to calculate a gain value as a function of information from the transducer. A display connects with the processor. The display is operable to display an image responsive to the gain value. The processor, the transducer, and the display are part of a handheld ultrasound system weighing less than about six pounds. A user input of the handheld ultrasound system is free of gain inputs for different depths.

In a second aspect, a method of automatic gain control is provided in medical diagnostic ultrasound imaging. An average of a frame of ultrasound data calculated regardless of a type of reflector. A gain factor is determined as a function of the average. Signals are amplified in an analog and digital domain as a function of the gain factor. An image responsive to the amplifying is generated.

In a third aspect, a computer-readable medium has stored therein instructions executable by a processor for automatic gain control in ultrasound imaging. The instructions include receiving a frame of log-compressed ultrasound data representing an entire scanned region, storing a sum of all of the log-compressed ultrasound data, calculating an average as a function of the sum, and determining a gain as a function of a difference of the average from a target value.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The time gain control (TGC) (also known as depth gain control) calculation automatically adjusts to generate a more uniform brightness while imaging. One or more exam specific TGC curve calculations are based on the type of imaging being done (e.g., pulse frequency, harmonic operation, B-mode, Color flow, and/or others). An overall gain factor is used as part of or with the TGC curve to change the perceived image brightness. This overall gain is driven by a feedback loop that adjusts the overall gain to make the image data "brightness" match a desired target. The "brightness" is calculated by creating an average, possibly spatially weighted, of the range data for multiple beams in the image. In one embodiment, the generation of the sum of range data for all imaging beams is done in hardware to avoid the time consuming calculation in software.

On a handheld ultrasound imaging machine, it is highly desirable to have a simple automatic function. Less skill from the operator is required to quickly produce a readable image. The focus in a handheld device may be to generate an image in the shortest time and with minimal effort rather than using time and effort for the most optimal image possible. The non-dominant hand may be holding the imaging unit, and the other hand may be controlling the probe. Complex physical and software user interface controls are awkward to manipulate. The TGC potentially requires modification each time the probe is moved, such as gel is displaced. Automatic control may avoid constant, difficult resetting. Minimal CPU processing power may be available. A simple and fast algorithm may allow execution on a low power/capability CPU.

Figure 1:
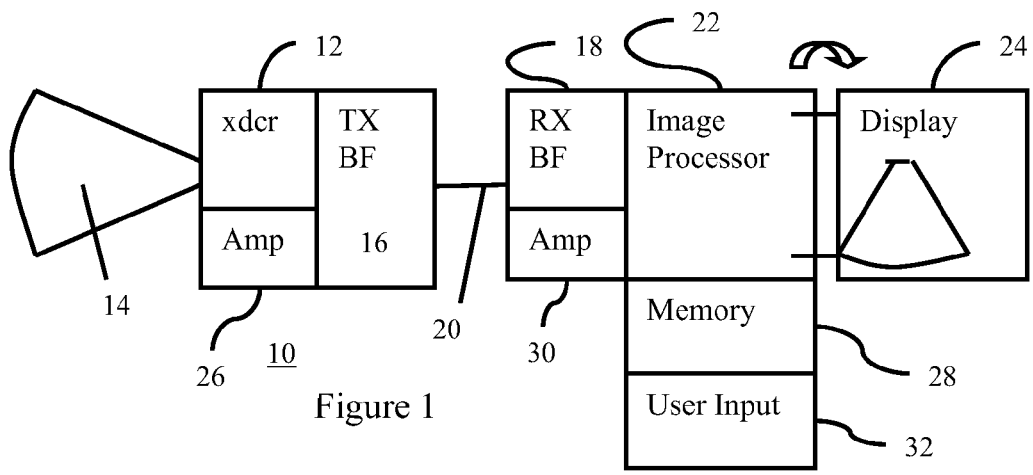
FIG. 1 is a block diagram of one embodiment of a medical diagnostic ultrasound imaging system for automatic gain control.
Figure 2:
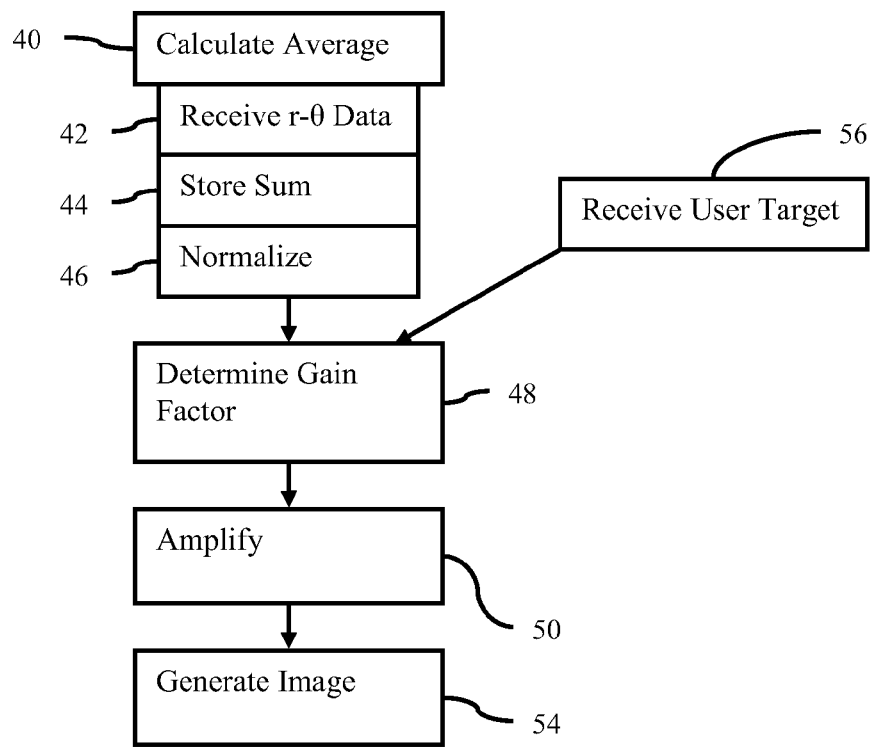
FIG. 2 is a flowchart of one embodiment of a method for automatic gain control.

FIG. 1 shows one embodiment of a medical diagnostic ultrasound imaging system 10 with automatic gain control. Any known or future dedicated ultrasound imaging system may be used. In other embodiments, the ultrasound imaging system 10 may be a computer, a workstation, a server, and/or an image database system for medical diagnosis with ultrasound images.

In one embodiment, the imaging system 10 is a cart-based imaging system. In another embodiment, the imaging system 10 is a portable system, such as a briefcase-sized system or laptop computer-based system. Other embodiments include handheld ultrasound systems. For example, one or more housings are provided where the entire system 10 is small and light enough to be carried in one or both hands and/or worn by a user. The processors 22, transducer 12, display 24, and/or other components are provided in a single housing. In another example, the transducer 12 is in one housing to be held by a person, and the imaging components and display 24 are in another housing to be held by the person. Coaxial cables connect the two housings. As another example, the transducer 12 and imaging components are in one housing, and the display 24 is in another housing. In yet another example shown in FIG. 1, the transducer 12 is in one housing connected by a cable 20 to a housing for the imaging components, including the image processor 22 and user input 32, and the display 24 is in a third housing hinged or rotatably connected with the housing of the image processor 22.

In any embodiment, the entire handheld system may weigh less than about 6 pounds, but may weigh more. For example, the handheld system weighs less than about 2 pounds (e.g., 1.6 pounds), a weight similar to commonly used, portable medical equipment and more naturally born by medical professionals without burden. "About" allows for manufacturing tolerances. The size of the handheld device may allow placement in a shirt or lab coat pocket.

The weight and size may be achieved by integrating the imaging functions into a limited number of chips or small scale circuits, such as processors, field programmable gate arrays, and/or application specific integrated circuits. For example, one or a few analog application specific integrated circuits are provided adjacent the transducer for transmit operation and channel reduction on receive. One or a few analog-to-digital converter chips connect with one or a few field programmable gate arrays implementing receive beamforming, filtering, detection, and scan conversion. A battery powers the system.

The system 10 includes a transducer 12, analog amplifiers 26, a transmit beamformer 16, a cable 20, digital amplifiers 30, a receive beamformer 18, an image processor 22, a display 24, a user input 32, and a memory 28. Additional, different, or fewer components may be used. For example, the cable 20 connecting the transducer 12 to the receive beamformer 18 is not provided, and/or a cable connects the display 24 to the image processor 22. Other locations for the analog and/or digital amplifiers may be provided. While shown as separate, different components may be integrated together on a same device or devices.

The transducer 12 is an array of elements. Any array may be used, such as a linear, phased, curved linear, or other now known or later developed array. Any number of elements may be used, such as 64, 96, 128, or other numbers. One, two, or other multi-dimensional (e.g., 1.25D, 1.5D, or 1.75D) arrays may be provided.

The elements are piezoelectric or capacitive membrane elements. A single layer of transducer material is provided for each element. Alternatively, the elements are multi-layered, such as having at least two layers of piezoelectric ceramic transducer material. The transducer material may be a semiconductor substrate with one or more flexible membranes (e.g., tens or hundreds for each element) formed within or on the semiconductor substrate. The transducer elements may also include any number of different layers, such as matching layers, flex circuit layers, signal traces, electrodes, a lens and/or a backing block.

The transducer 12, for example, is in an ultrasound probe connected with an ultrasound system or is in a housing for the entire system 10. The transducer 12 connects with the transmit beamformer 16.

The transmit beamformer 16 connects with electrodes on one side of the elements, and the receive channels connect with electrodes on an opposite side of the elements. Passive or active switching grounds the electrodes not being used, such as grounding transmit side electrodes during receive operation. Alternatively, the transmit and receive beamformers 16, 18 connect to the transducer 12 through a transmit/receive switch.

The transmit beamformer 16 is a plurality of transistors, such as high power transistors for generating relatively delayed unipolar or bipolar waveforms. Amplifiers, delays, phase rotators, waveform generators, memories, or other components may be provided for focusing and/or apodization.

In response to signals from the transmit beamformer 16, the transducer 12 generates acoustic beams. The acoustic beams are focused to different locations to scan a two or three-dimensional region 14. The scan format is linear, sector, Vector®, or other now known or later developed scan format. The scan format includes a set or programmable number of beams within the region 14, such as 50-150 beams. The depth of the region 14 may be set or programmable.

The transducer 12 is operable to receive acoustic signals and convert the acoustic signals into electrical energy. For example, the transducer 12 is operable to acquire ultrasound signals by receiving echo signals. The ultrasound signals include information for C-mode (e.g., Doppler mode, flow mode, velocity, energy, or variance), B-mode (grey-scale), and other tissue or flow information.

The transducer 12 connects with the analog amplifiers 26. Each element of the transducer 12 connects with an analog amplifier 26. The analog amplifiers are pre-amplifiers. The analog amplifiers 26 may have a fixed gain. Alternatively, the analog amplifiers 26 are programmable to alter the gain as a function of time for depth gain control and/or as a function of an overall gain. Control signals indicate the gain at a given time. The analog amplifiers 26 are separate components or are integrated in groups into an integrated circuit.

Other components may be integrated with the analog amplifiers 26 or connect with the amplifiers 26 from separate integrated circuits. For example, multiplexers provide for aperture control to connect elements to different channels at different times. To reduce a number of cables, the number of connections from the elements to the receive beamformer 18 may be reduced. Time multiplexing, frequency multiplexing, sub-array mixing, partial beamforming or other processes for combining signals may be used. For example, signals from groups of four or other numbers of elements are combined onto common data paths by sub-array mixing, such as disclosed in U.S. Pat. No. 5,573,001 or U.S. Published Application No. 20040002652, the disclosures of which are incorporated herein by reference. The channel reduction occurs adjacent the transducer 12, such as between the transducer 12 and the cables 20. In other embodiments, channel reduction is not provided.

The amplified electrical signals from the transducer 12 are provided via the coaxial or other cables 20 to analog-to-digital converters (ADC). The ADCs are any known or future analog-to-digital converters operable to sample analog signals, such as echo signals. For example, ADCs connect with respective elements (channels) of the transducer. The ADCs output digital information from the transducer 12.

The digital information is received by the digital amplifiers 30. The digital amplifiers 30 are processors, filters, multipliers, amplifiers, or other digital component for increasing and/or decreasing the gain of the received information. The digital amplifiers 30 are programmable for altering an amount of gain. Using a table or other structure, control signals control the gain as a function of time. Depth gain control is provided by, at least in part, by the digital amplifiers 30. The digital amplifiers 30 may be located after the receive beamformer 18 or separated into stages at different locations in the processing path. In one embodiment, the digital amplifiers 30 are implemented in a same device as the receive beamformer 18, such as a processor (e.g., field programmable gate array). In other embodiments, the digital amplifiers 30 are separate integrated circuits.

The receive beamformer 18 is a digital beamformer. The receive beamformer 18 is an application specific integrated circuit, processor, field programmable gate array, digital components, integrated components, discrete devices, or combinations thereof. The receive beamformer 18 includes, but is not limited to, amplifiers, delay memories, a delay calculator, a phase rotator, a demodulator, a baseband filter, and/or channel adders for forming beams.

The receive beamformer 18 receives digital information for the elements or groups of elements from the digital amplifiers 30. The receive beamformer 18 apodizes and relatively focuses the received samples. Electrical signals received from the transducer elements are relatively delayed and summed. Amplifiers may be provided for apodization, or the digital amplifiers 30 are used. In one embodiment, the delays are implemented as memories for storing channel data (e.g., samples from each element). One or more memories may be used. For example, two memories or sets of memories operate in a ping-pong fashion to store data from elements and read data out for beamforming. Each memory or set stores element data for an entire scan. As one memory or set is storing, the other memory is outputting. By reading data out of the memory from selected memory locations, data associated with different amounts of delay is provided. The same data may be used for sequentially or parallel forming receive beams along different scan lines. Other memories may be used, such as a plurality of first-in, first-out buffers for delaying based on length and/or timing of input into the buffers.

Other components may be provided separate from or implemented on a same device as the receive beamformer 18. For example, filters are provided for spatial and/or temporal filtering beamformed data. As another example, decimators are provided. In other examples, filters for filtering coherent data (prior to detection) are provided.

The image processor 22 receives the beamformed information from the transducer 12. The image processor 22 is implemented by a general processor, control processor, digital signal processor, application specific integrated circuit, field programmable gate array, digital circuit, memory, combinations thereof, or other now known or later developed processor. In one embodiment, the processor 22 is a single device. In other embodiments, the processor 22 includes a plurality of devices, such as distributed processors.

The image processor 22 implements detection, filtering, scan converting, or combinations thereof. The same hardware operating under different code may implement the different operations of the image processor 22, but separate devices may be used. In one embodiment, the image processor 22 includes a B-mode detector and a Doppler estimator. The B-mode detector determines an intensity of the echo signals. The envelope or other characteristic of the receive beamformed data responsive to tissue, fluid or other reflector is detected. The detection is performed for an entire scan or a frame of data for one image. The Doppler estimator estimates velocity, power, variance or combinations thereof for a region of interest. A clutter filter may be provided to isolate information for slowly moving tissue or more rapidly moving fluid. The estimation is performed for a region on data separate from or in addition to the data used for B-mode detection.

The image processor 22 may include a persistence filter, spatial filters, log compressor, scan converter, or combinations thereof. For example, detected data is persisted and log compressed. The log-compressed data is scan converted. The scan conversion converts the r-θ or polar coordinate data into a Cartesian coordinate format for the display 24.

The image processor 22 is operable to control gain applied by the analog amplifiers 26 and/or the digital amplifiers 30. For example, the image processor 22 is a same device for calculating a gain value and a time gain curve as a function of the gain value, perform ultrasound detection, and perform filtering. The different functions are scheduled. Any scheduling may be used. In one embodiment, the gain control has a lower priority. Accordingly, gain control calculations are performed when the image processor 22 is not performing other, higher priority functions. This may result in more intermittent or longer periods between updating the gain value and/or time gain curves. Alternatively, the gain control function has a higher priority or is implemented on a separate device.

The image processor 22 calculates the gain value as a function of information from the transducer 12. Channel data before beamforming or data from other locations in the processing pipeline may be used. In one embodiment, the information from the transducer 12 used for calculating gain is data prior (i.e. r-θ data) to conversion to color (e.g., RGB) for the display 24 and/or prior to scan conversion. For example, log compressed, detected, and filtered data is fed back for calculation of the gain value.

The gain value is determined to bias a resulting brightness to a target level. The gain value is then incorporated into the gain applied by the analog and/or digital amplifiers 26, 30.

Samples representing a scanned region are summed. The samples are B-mode, Doppler (color) mode, or other modes. The samples to be used are summed regardless of the type of reflector. For example, B-mode values associated with tissue response are not isolated from B-mode values associated with fluid response. The B-mode detection and filtration may increase the likelihood of values representing tissue, but may not remove data from other reflectors. Data from fluid may be reduced or even set to a noise level or less, but may still be included in the calculation of average. Noise information may or may not be removed. Alternatively, data from desired reflectors is identified and used, and data from other locations is not used. The summed samples represent the entire scanned region, such as being all the values in a frame of data. Alternatively, samples from different spatial locations may be used, such as using only some scan lines, groups of lines, some depths, groups of depths, combinations thereof, or other spatial distribution made regardless of the actual type of reflector represented by the data.

The sum is stored in the memory 28 or another memory associated with the image processor 22. For example, a register is used to provide a hardware based sum to minimize processing usage. Software based sums may be used.

The sum is normalized. An average is calculated. The average is of all or a sub-set of the samples in a frame of data representing the scanned region. The scanned region is the region used for imaging, such as a sector or Vector® region.

The gain value is a determined as a function of the average or other value calculated from data and a target value. For example, a target brightness is preset. In one embodiment, the target brightness is input by the user before or during imaging.

A difference between the image brightness and the target brightness is calculated. For example, a difference between the target value and the average value is determined. The gain value is set based on the difference. A greater difference provides a greater gain off set.

In one embodiment, other limitations are placed on the gain value. If the difference is small, such as below a threshold, then the gain value may be unity or other value associated with no change in bias.

The image processor 22 uses the gain value to offset the depth gain curve or curves. The depth gain curve is determined based on any desired formula. For example, the curve may be different for harmonic or higher frequency operation due to the differences in attenuation as a function of frequency. As another example, hardware instability may be compensated or avoided by more rapid or less rapid ramping initially, at the end, or in the middle of the depth gain curve (e.g., a near field ramp-up to avoid ringing may be included). Any considerations may be used for determining the gain curve.

The gain curve is offset by a gain. The offset gain is the gain value or a value derived from the gain value. For example, the gain value is adjusted to compensate for log compression and/or other processing between application of the amplification and the data used to determine the gain value. The gain offset may be applied along the entire depth gain curve. Alternatively, limits on the depth gain curve continue to apply, so that the gain off set is applied to only portions of the curve, is reduced, or is increased.

The determined gain for each depth programs the analog, digital or both analog and digital amplifiers 26, 30. The amplifiers 26, 30 operate as a function of the gain value. For example, the imaging processor 22 populates a table for each of the digital and analog amplifiers 26, 30. The analog amplifiers 26 may be limited in total gain due to saturation. Other limitations may apply. The gain appropriate for the analog amplifiers 26 is determined. The remaining gain is applied by the digital amplifiers 30. Other separation criteria may be used. The tables indicate the gain to be applied by the amplifiers 26, 30 for information as each given depth. Lateral gain differences may also be applied.

The user input 32 includes a button, a keyboard, a rocker, a joystick, a trackball, a voice recognition circuit, a mouse, and/or any other input device for sending commands in response to user activation. In one embodiment, the user input 32 includes a trackball surrounding by buttons and a keyboard below the trackball and buttons. In a handheld device, the user input 32 is on one a housing to be held by the user, such as the transducer, display, or image processor housing.

The user input 32 may be used to set the target brightness. The user rotates a knob, operates a touch screen, scrolls with a trackball or buttons, or uses other +/−devices to increase or decrease the target brightness. The current images may also increase or decrease in brightness based on the change of the target value. Subsequent images may also be brighter or less bright due to the setting of the target value. The target value may be maintained even after powering off the system 10 or is reset each time the system 10 is powered on. The target value may be maintained through other changes, such as a change in scanning depth, so that the overall brightness is perceived to be the same. The target value may be the same or different for different types of examination, such as harmonic, fundamental, or color exams. In other embodiments, the target value is programmed by the manufacturer, loaded as software, or otherwise preset.

The automatic gain may avoid depth gain control sliders or other inputs on the user input 32. Such sliders or inputs are space consuming and/or difficult to implement with one hand, especially where the one hand is holding a portion of the system 10 and is the user's non-dominant hand. Alternatively, depth gain inputs are provided, such as with a touch screen.

The display 24 is a liquid crystal display, monitor, plasma screen, projector, printer, combinations thereof, or other now known or later developed display device. In one embodiment, the display 24 includes pixel locations arranged in a grid. Each pixel location includes red, blue, and green light sources. Each color light source is a color component of the display. By using different intensities or brightness for each color component, a color and brightness is output from the pixel. The user visually integrates the components into a perceived color and brightness for each pixel. Any range of incremental levels may be used for each color component, such as 6-bit, 8-bit, 12-bit or others. The range for each color component is the same or different. The colors are mapped from the gain-adjusted information, such as the r-θ data before scan conversion or scan converted data. The gain adjustments result in different assignment of color levels and corresponding brightness. Displays with different color components, distribution of color sources other than per pixel, or other display formats or pixel distributions may be used.

In one embodiment, the display 24 is a small, digital LCD, such as associated with handheld devices (e.g., cellular phones or personal data assistants). For example, the display 24 is less than 10 inches along a longest dimension, such as being about 3×4 inches. Any number of pixels may be provided. In alternative embodiments, the display 24 is larger, such as associated with personal computers, laptop computers, or television displays.

The display 24 operates to generate an image from data provided by the image processor 22. The display 24 receives scan converted ultrasound data and displays an image. An image is generated for each frame of data. For real-time ultrasound imaging, the display 24 receives frames of data and displays a sequence of ultrasound images each representing the region 14 or overlapping portions thereof. The images are responsive to the gain value, such as having increased or decreased brightness.

The memory 28 is a logic encoded medium having stored therein data representing executable instructions for automatic gain control. For example, software is stored and executable by a processor. The instructions for implementing the processes, methods and/or techniques discussed herein are provided on computer-readable storage media or memories, such as a cache, buffer, RAM, removable media, hard drive or other computer readable storage media. Logic encoded storage media include various types of volatile and nonvolatile storage media. The functions, acts or tasks illustrated in the figures or described herein are executed in response to one or more sets of instructions stored in or on logic encoded storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. In another embodiment, the memory 28 is within a handheld ultrasound system with one or more housings.

FIG. 4 is a flowchart of one embodiment of a method of automatic gain control in medical diagnostic ultrasound imaging. The method is implemented with the system 10 of FIG. 1, or other ultrasound imaging system. For example, the method is performed with a handheld ultrasound system weighing less than two pounds. The calculating, determining, amplifying, and generating are performed in the handheld ultrasound system without depth-based user gain control. In other embodiments, other systems perform one or more of the acts and/or user control of depth gain is provided. The method is performed in the order shown or another order. Additional, different, or fewer acts may be performed. For example, act 56 is not provided.

Ultrasound data for generation of an image is acquired. For example, C-mode and/or B-mode data is acquired using a transducer. Prior to or during acquisition, the depth gain curve is determined. The depth gain curve is a function of a gain value. The method is performed in response to time, changes in imaging, power on, user activation, processor availability, and/or combinations thereof. The method is performed once or repeated, such as at about 2-10 Hz. For example, the TGC calculation is constantly being updated during imaging to maintain a desired average brightness.

In act 40, a feedback value from the ultrasound data is calculated. For example, an average is calculated. The average is of the data from a frame of data, such as all or any spatial sub-set of a frame of data. An average from a plurality of frames may be used. The average is calculated from samples, regardless of the type of reflector.

The feedback is determined from data along any portion of the data pipeline. In act 42, r-θ (polar coordinate data) is extracted or received for determining the average. For example, the data after processing but before color mapping and scan conversion is used. An average of persisted, log compressed ultrasound data prior to color conversion is calculated from an entire scanned region or a portion of the scanned region.

To calculate the average feedback value, a sum of the ultrasound data is determined and stored in act 44. For example, an entire frame of data of log-compressed data is summed and stored.

In act 46, the sum is normalized. The sum is divided by the number of samples used in the sum. The normalized sum is an average. A weighted average may be used, such as weighting data from different locations in the frame of data. The different locations may be preset or based on data. The average may be either a non-weighted average of range data for all beams, an average of range data of a set of beams (i.e. every n'th beam), a combination (i.e. all center beams and a set of specified edge beams), or other spatial grouping. Different weights for the range data may be used, such as to cause the center data to have greater weight in the average or avoid a known near/far field structure. The average calculation can be changed for different imaging modalities as desired.

In act 48, a gain factor is determined. The gain factor is a function of the feedback value, such as a function of the average. The gain factor is a weight, gain offset, actual gain, or other gain associated value. In one embodiment, the gain factor is an offset determined as a function of a difference between the average and a target value.

In one embodiment, algorithm control variables are defined as follows:

| | |
|---|---|
| target | desired image average value |
| deadband | threshold for ignoring changes in average |
| scale | converts average difference to dB change |
| gain_offset | Offset gain for TGC calculation |
| gain_low | dB lower limit for TGC gain calculation |
| gain_high | dB upper limit for TGC gain calculation |
| average | Generated image data average |

Given these variables, an example update algorithm is:

```
difference = abs(average – target)
if (difference > deadband) then
    step = difference / scale
    if (step < 1) then step = 1
    if (average > target) then
        if (gain_offset > gain_low) then
            gain_offset = gain_offset – step
        end if
    else
        if (gain_offset < gain_high) then
            gain_offset = gain_offset + step
        end if
    end if
end if
```

Calculate New TGC Curve based on gain_offset if it changed

In act 50, information is amplified. The gain offset controls an amplifier to increase or decrease the overall gain. The offset may be applied to or in a time gain control curve. In one embodiment, the gain offset is distributed between amplification in an analog and a digital domain. Alternatively, the gain offset is applied in just the analog domain or just the digital gain.

In act 52, an image is generated. The image is responsive to the amplifying. The image is generated with a substantially target brightness. When the average brightness is less than or more than the target, the gain is increased or decreased to provide an image closer to the target brightness.

In one embodiment, the calculating (act 40), determining (act 48), and amplifying (act 50) are performed by a same processor as the generating (act 52). For example, the algorithm is run constantly as a separate task on the device processor with a priority less than that of the user interface management. This causes the task to update as fast as possible—approximately every 0.25 to 0.5 seconds—unless the user is making modifications where the update rate slows as necessary.

In act 56, the target value or brightness is set. The target is set based on prior programming, or in response to user input. For example, the user adjusts a knob or other input during, before, or after imaging.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system for automatic gain control in medical diagnostic ultrasound imaging, the system comprising:
   a transducer;

a processor connected with the transducer, the processor operable to calculate a gain value as a function of information from the transducer;

a display connected with the processor, the display operable to display an image responsive to the gain value;

wherein the processor, the transducer, and the display are part of a handheld ultrasound system weighing less than about six pounds; and a user input of the handheld ultrasound system being free of any depth gain inputs for different depths, the gain value calculated by the processor without depth gains from the user input, the image being free of response to any depth gains from the user input.

2. The system of claim 1 wherein the user input is free of sliders associated with depth gain adjustment as the gain inputs for the different depths, the user input comprising variable input for a target brightness, the gain value being a function of a difference between the target brightness and an image brightness associated with the information from the transducer.

3. The system of claim 1 wherein the information from the transducer comprises detected information prior to conversion to color for the display.

4. The system of claim 3 wherein the information from the transducer comprises detected information prior to scan conversion.

5. The system of claim 1 wherein the processor is operable to calculate the gain value from samples representing the scanned region regardless of a type of reflector represented by the samples.

6. The system of claim 5 wherein the processor is operable to calculate an average of all samples in a frame of data representing a scanned region, the frame of data being based on the information from the transducer.

7. The system of claim 1 further comprising an analog amplifier connected with the transducer, and a digital amplifier in a beamformer, the analog and digital amplifiers operating as a function of the gain value.

8. The system of claim 1 wherein the handheld ultrasound system weighs less than about two pounds.

9. The system of claim 1 wherein the display comprises a digital liquid crystal display, and wherein the handheld ultrasound system comprises a first housing for the transducer, a second housing for the processor, and a third housing for the display, the first and second housings connected by a cable, and the third housing being rotatably connected with the second housing.

10. The system of claim 1 wherein the processor comprises a single device, the processor being operable to calculate a time gain curve as a function of the gain value, perform ultrasound detection, and perform filtering.

11. The system of claim 1 wherein the processor comprises a register operable to store a sum of the information from the transducer.

12. A method of automatic gain control in medical diagnostic ultrasound imaging, the method comprising:

calculating an average of a frame of ultrasound data;

determining a value of a gain factor as a function of the average and without accounting for different types of reflectors represented in the frame of the ultrasound data;

amplifying ultrasound signals, received subsequent to the frame of ultrasound data, in analog and digital domains as a function of the gain factor; and generating an image responsive to the amplifying of the signals.

13. The method of claim 12 wherein calculating comprises calculating a single average for the frame of the ultrasound data, all of the ultrasound data of the frame weighted equally in the single average, and wherein determining comprises determining the gain factor as a single value and as a function of the single average.

14. The method of claim 12 wherein the ultrasound data comprises persisted, log compressed ultrasound data, and wherein calculating an average comprises calculating an average of the persisted, log compressed ultrasound data prior to color conversion.

15. The method of claim 12 wherein calculating an average comprises calculating an average of all data in the frame.

16. The method of claim 12 wherein determining the gain factor comprises determining a gain offset as a function of a difference between the average and a target value.

17. The method of claim 12 wherein generating the image comprises generating the image with a substantially target brightness, the gain factor being a function of the target brightness.

18. The method of claim 12 wherein the calculating, determining, amplifying and generating are performed in a handheld ultrasound system weighing less than two pounds and free of depth-based user gain control.

19. The method of claim 12 wherein the calculating, determining, and amplifying are performed by a same processor as the generating.

20. In a non-transitory computer-readable medium having stored therein instructions executable by a processor for automatic gain control in ultrasound imaging, the instructions comprising:

receiving a frame of log-compressed ultrasound data representing an entire scanned region;

storing a sum of all of the log-compressed ultrasound data, the sum of all of the log-compressed ultrasound data being determined prior to any calculating of any average for determining a gain from the log-compressed ultrasound data of the frame;

calculating an average as a function of the sum and a number of samples of the all of the log-compressed ultrasound data;

determining the gain as a function of a difference of the average from a target value; and generating an image as a function of the gain.

21. The non-transitory computer-readable medium of claim 20 wherein the instructions further comprise adjusting analog and digital gain curves as a function of the gain.

* * * * *